United States Patent [19]

Saman

[11] Patent Number: 4,775,631

[45] Date of Patent: Oct. 4, 1988

[54] METHOD OF LOCALIZING NUCLEIC ACIDS BOUND TO POLYAMIDE SUPPORTS

[75] Inventor: Eric L. J. Saman, Bornem, Belgium

[73] Assignee: Janssen Pharmaceuitica, N.V., Beerse, Belgium

[21] Appl. No.: 759,562

[22] Filed: Jul. 26, 1985

[51] Int. Cl.$^4$ ............................................. C12N 15/00
[52] U.S. Cl. ...................................... 435/6; 436/501; 935/77; 935/78; 935/87
[58] Field of Search ................ 435/6; 935/77, 78, 87; 436/501

[56] References Cited

U.S. PATENT DOCUMENTS 4,455,370  6/1984  Bartelsman ............................ 435/6

OTHER PUBLICATIONS

Moeremans, Analytical Biochemistry 145, 315–321 (1985).

Primary Examiner—Robert J. Warden
Assistant Examiner—Robert Benson
Attorney, Agent, or Firm—Geoffrey G. Dellenbaugh

[57] ABSTRACT

A method of detecting and localizing nucleic acids on polyamide supports which comprises contacting said supports with a suspension of colloidal metal particles whereupon the metal particles bind to the polyamide support and form a colored background against which the location where nucleic acids are present become visible as lighter spots. The method enables the mere qualitative localization of the nucleic acids and the quantitative determination thereof following art-known procedures.

8 Claims, No Drawings

METHOD OF LOCALIZING NUCLEIC ACIDS BOUND TO POLYAMIDE SUPPORTS

Detection of unlabeled nucleic acids, e.g. after electrophoretic separation in agarose or polyacrylamide gel system, is routinely performed using ethidiumbromide staining and ultraviolet illumination. However, thus far, no useful method for the detection of unlabelled nucleic acids on polyamide (i.e. nylon based) transfer membranes is available. Such membranes are routinely used for the transfer and hybridization of nucleic acids. Consequently, in the present state of the art, a thorough evaluation of the transfer process is often difficult and unreliable since no direct comparison of the hybridization pattern with the complete nucleic acid pattern of the preparation can be made. Such can easily be done following the method according to the invention which combines a remarkable ease of operation with an excellent sensitivity.

Nucleic acids as referred to herein are meant to include both ribonucleic acids (RNA) and desoxyribonucleic acids (DNA). Polyamide supports to which the method according to the invention can be successfully applied include any type of polyamide material to which nucleic acids can be fixed either directly (dot spot) or by transfer from gel supports by the so-called blotting technique. In the specialized literature, blotting of DNA is usually referred to as "Southern" and blotting of RNA as "Northern" blotting.

Examples of polyamide or nylon based membranes to which the method can be successfully applied include the polyhexamethylene adipamide polymers which are available from various manufacturers and under various tradenames.

Metals which may be used in the present technique are essentially those of which stable colloids can be prepared and which under the relevant pH conditions are positively charged. Examples of such metals are gold, platinum, silver and copper, gold being preferred. The particle size of the colloidal metal particles may vary within wide limits but is preferably comprised between 1 and 100 nm. The appropriate pH is preferably the pH at which binding of the colloid to the polyamide membrane is maximal, i.e. when the colloidal metal particles and the membrane have opposite net charges. Adjustment of the pH can be achieved in any of the usual ways. Addition of a stock buffer to about a 10 mM final concentration to the colloidal metal particles is a preferred method. The appropriate concentration of the colloidal metal particles is one that gives a uniform and easily discernable colouration of the polyamide background within practical incubation times (from few minutes to about one day). It can be obtained by appropriately choosing the proper concentrations of the starting materials with which they are prepared, or by dilution or concentration by art-known methods.

Compared with the presently available techniques, the method according to the invention has important advantages.

The method allows fast and sensitive detection of nucleic acids, fixed on widely used nylon based membranes. This can be advantageous, when comparing hybridization patterns on autoradiographs with a complex banding pattern of the preparation. Direct superposition of both images allows direct localisation of the hybridizing fragments. Moreover, the staining allows quantitative and qualitative evaluation of the transfer process, without the need to include radiolabelled markers. Since staining is roughly proportional to the amount of nucleic acid fixed, one can make an estimation by comparing with a standard dilution series stained in parallel.

In view of its sensitivity and ease of operation, the method according to the invention has a wide field of applications. In principle it can be used in any circumstances where localisation of nucleic acids on nylon based membranes is desired.

Such is, for example, currently done in connection with nucleic acid sequence determinations which is largely based on the splitting of DNA or RNA chaines with specific enzymes, separation of the fragments formed by electrophoretic techniques and subsequent identification of the separated fragments, e.g. by means of hybridization. Nucleic acid sequence determinations are becoming more and more important as a tool in genetic engineering research and development.

The method may also find application in the field of clinical diagnosis, more particularly, when the presence of certain specific nucleic acids in biological specimens are indicative for certain pathological conditions, e.g. genetic aberration.

The invention is further illustrated by the following examples which are not intended to limit the scope thereof.

EXAMPLES

Materials and Methods

Reagents:

All reagents were of the highest available quality. Bovine serum albumine (BSA) (fraction V) was obtained from Boehringer Mannheim. Plasmid DNA, used in these experiments, was purified by two rounds of CsCl purification and was essential free of RNA. Anionic stabilized colloidal gold solution (Auro-dye) was from Janssen Chimica (Belgium) and had a particle size of 20 nm mean diameter (for description see Moeremans et al. in Jour. Anal. Biochem. 145, (1985) p.315–321.)

Membranes:

In our experiments, we routinely use Pall Biodyne A membranes. The method has however, also been tested on Gene Screen membranes (NEN).

Dot spot procedure:

Samples of solutions (usually 1 μl), containing different concentrations of nucleic acids, were applied on the filter and air dried. Subsequently, the filters were either baked (80° C., 1 hour) or treated with denaturing solution (0.5M NaOH; 1.5M NaCl) and neutralizing solution (3M Na acetate, pH 5.8) for five minutes each, prior to baking. Denaturation and neutralization were performed by placing the filters (side of application upward) onto a piece of Whatman 3 MM paper, saturated with the relevant solution.

Southern transfer:

Was performed essentially as described by Maniatis, T., Fritsch, E. F. and Sambrook, J. ((1982) Molecular cloning: A Laboratory Manual, Cold Spring Harbor, New York, Cold spring Harbor Laboratory, p. 383–386). After separation of the DNA in agarose gel (1.4%) and staining with ethidiumbromide, the gel was incubated in denaturing solution (30 min) and subsequently in neutralizing solution (30 min). The gel was then blotted dry and placed onto sheets of Whatman 3 MM paper, saturated with 20×SSC (3M NaCl, 0.3M Na citrate, pH 7.0) and soaked into 20×SSC solution at two opposing ends. A piece of Biodyne A membrane was placed on top of the gel and covered with dry paper towels. Transfer was allowed to proceed overnight. The filter was then removed and air dried before baking (80° C., 1 hour).

Staining procedure

Auro-dye:

After the baking, the membranes are briefly washed in 0.2% Tween 20 solution (3 times, 5 min) and then incubated in the Auro-dye solution with the application side down. The solution is agitated gently for several hours, until the membrane is stained intensely red. Overnight staining is recommended, when possible. It may also be necessary to replace the Auro-dye solution after a few hours. Finally the membrane is washed with water and dried. It was found that 0.1 $\mu$g of DNA could easily be detected when applied in 1 $\mu$l of solution (covering about 3-4 mm$^2$). When RNA was used, about 0.5 $\mu$g of ribosomal RNA could be detected when applied in a similar way. It was also shown that the sensitivity for detection on Gene-screen membranes was comparable with that on Pall Biodyne A, both for RNA and DNA.

What we claim is:

1. A method of localizing nucleic acids on polyamide supports which comprises contacting said supports with an aqueous suspension of colloidal metal particles whereupon the metal particles bind to the polyamide support and form a coloured background against which the locations where nucleic acids are present become visible as lighter spots.

2. A method according to claim 1 wherein the colloidal metal particles are gold particles.

3. A method according to claim 2 wherein the gold particles have a mean diameter between 1 and 100 nm.

4. A method according to any one of claims 1 to 3 wherein the said nucleic acids are deoxyribonucleic acids.

5. A method according to any one of claims 1 to 3 wherein the said nucleic acids are ribonucleic acids.

6. A method according to any one of claims 1 to 3 wherein the said polyamide support is a polyhexamethylene adipamine.

7. A method according to claim 1 wherein the polyamide support is a nylon based membrane.

8. A method according to claim 7 wherein the colloidal metal particles are gold, platinum, silver, or copper particles.

* * * * *